United States Patent [19]

Han et al.

[11] Patent Number: 5,012,029

[45] Date of Patent: Apr. 30, 1991

[54] CONVERSION OF METHANE

[75] Inventors: Scott Han, Lawrenceville; Daniel J. Martenak, Trenton, both of N.J.; Robert E. Palermo, New Hope; Dennis E. Walsh, Richboro, both of Pa.

[73] Assignee: Mobil Oil Corp., Fairfax, Va.

[21] Appl. No.: 422,367

[22] Filed: Oct. 16, 1989

[51] Int. Cl.$^5$ ................................................ C07C 2/02
[52] U.S. Cl. .................................... 585/500; 585/658; 585/943; 568/910
[58] Field of Search ........................ 585/500, 658, 943; 568/910

[56]         References Cited
        U.S. PATENT DOCUMENTS

| | | | |
|---|---|---|---|
| 3,965,205 | 6/1976 | Garwood et al. | 585/409 |
| 4,433,189 | 2/1984 | Young | 585/408 |
| 4,497,970 | 2/1985 | Young | 585/417 |
| 4,618,732 | 10/1986 | Gesser et al. | 568/910 |
| 4,695,663 | 9/1987 | Hall et al. | 585/500 |

FOREIGN PATENT DOCUMENTS 2070325  3/1987  Japan ................................. 585/500

OTHER PUBLICATIONS

Shepelev, S. S. et al., Reaction Kinetic Catal. Lett., vol. 23, 3-4, pp. 323-325 (1983).

Primary Examiner—Asok Pal
Assistant Examiner—James Saba
Attorney, Agent, or Firm—Alexander J. McKillop; Charles J. Speciale; Edward F. Kenehan, Jr.

[57]           ABSTRACT

A mixture of organic compounds comprising a major amount of liquid hydrocarbons, mostly aromatic, is formed by the direct partial oxidation of methane in the presence of a ZSM-5 catalyst. The reaction conditions are substantially the same as those required for the direct homogeneous partial oxidation to methanol. However, liquid hydrocarbon formation depends on the presence of a small amount of an impurity such as propane or propylene in the feed; in the absence of such, only methanol is formed. With such modifier present, controls of reaction parameters, e.g., temperature, permits synthesis of both methanol and liquid hydrocarbons in desired proportions. Properly processed natural gas can serve to provide methane and at least part of the reaction modifier.

12 Claims, 1 Drawing Sheet

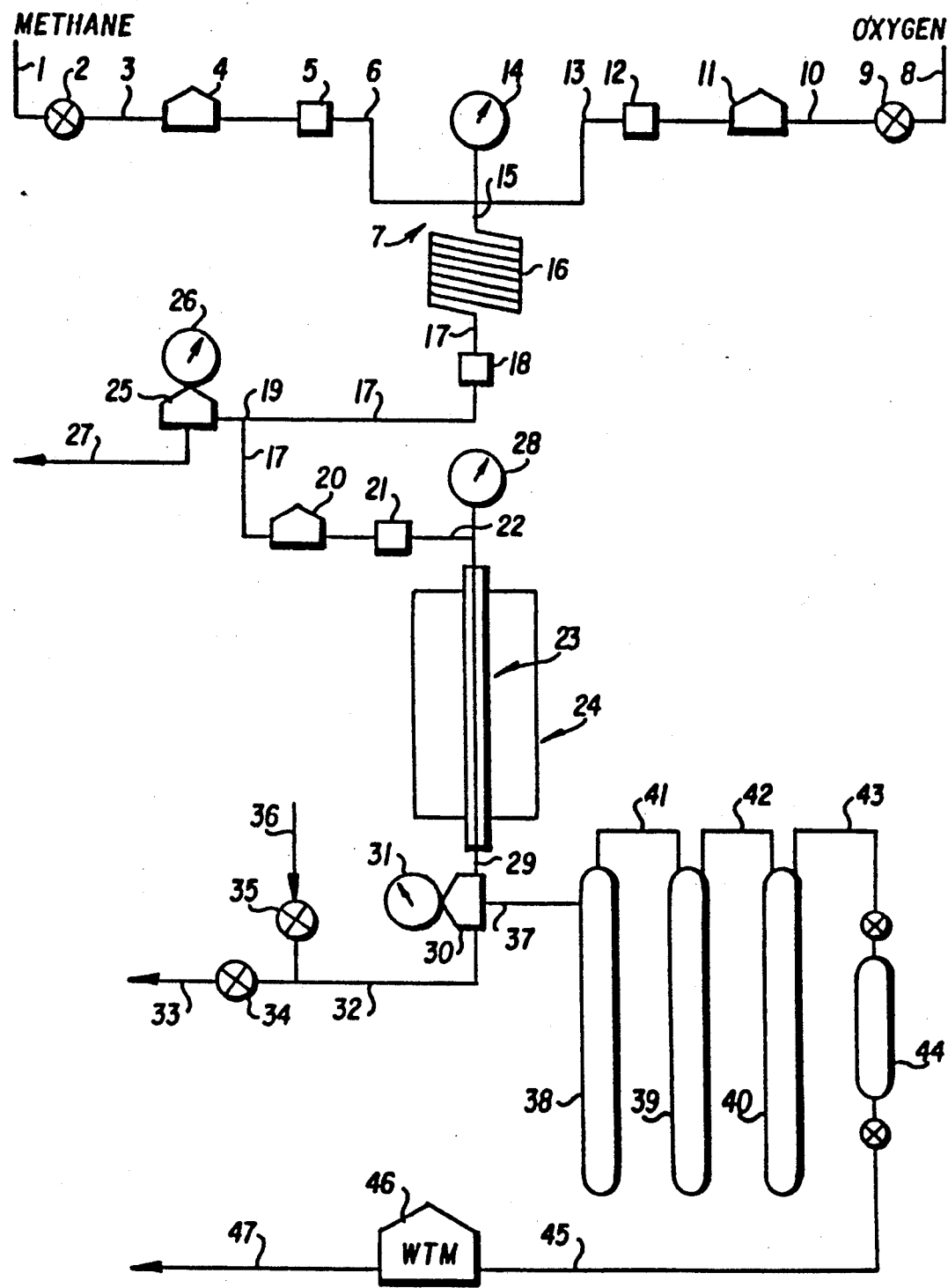

CONVERSION OF METHANE

FIELD OF THE INVENTION

This invention pertains to the direct partial oxidation of a gaseous feed comprising a source of methane to normally liquid products comprising liquid hydrocarbons. In one embodiment, it pertains to converting a gaseous feed comprising natural gas admixed with gaseous oxygen to normally liquid hydrocarbons.

BACKGROUND OF THE INVENTION

Natural gas is an abundant fossil fuel resource. Recent estimates places worldwide natural gas reserves at about $35 \times 10^{14}$ standard cubic feet, corresponding to the energy equivalent of about 637 billion barrels of oil.

The composition of natural gas at the wellhead varies but the major hydrocarbon present is methane. For example the methane content of natural gas may vary within the range of from about 40 to 95 volume percent. Other constituents of natural gas may include ethane, propane, butanes, pentanes (and heavier hydrocarbons), hydrogen sulfide, carbon dioxide, helium and nitrogen.

Natural gas is classified as dry or wet depending upon the amount of condensable hydrocarbons contained in it. Condensable hydrocarbons generally comprise $C_3+$ hydrocarbons although some ethane may be included. Gas conditioning is required to alter the composition of wellhead gas, processing facilities usually being located in or near the production fields. Conventional processing of wellhead natural gas yields processed natural gas containing at least a major amount of methane.

Processed natural gas, consisting essentially of methane, (typically 85-95 volume percent) may be directly used as clean burning gaseous fuel for industrial heat and power plants, for production of electricity, and to fire kilns in the cement and steel industries. It is also useful as a chemicals feedstock, but large-scale use for this purpose is pretty much limited to conversion to synthesis gas which in turn is used for the manufacture of methanol and ammonia. It is notable that for the foregoing uses, no significant refining is required except for those instances in which the wellhead-produced gas is sour, i.e., it contains excessive amounts of hydrogen sulfide. Natural gas, however, has essentially no value as a portable fuel at the present time. In liquid form, it has a density of 0.415 and a boiling point of minus 162° C. Thus, it is not readily adaptable to transport as a liquid except for marine transport in very large tanks with a low surface to volume ratio, in which unique instance the cargo itself acts as refrigerant, and the volatilized methane serves as fuel to power the transport vessel. Large-scale use of natural gas often requires a sophisticated and extensive pipeline system.

A significant portion of the known natural gas reserves is associated with fields found in remote, difficultly accessible regions. For many of these remote fields, pipelining to bring the gas to potential users is not economically feasible.

Indirectly converting methane to methanol by steam-reforming to produce synthesis gas as a first step, followed by catalytic synthesis of methanol is a well-known process. Aside from the technical complexity and the high cost of this two-step, indirect synthesis, the methanol product has a very limited market and does not appear to offer a practical way to utilize natural gas from remote fields. The Mobil Oil Process, developed in the last decade provides an effective means for catalytically converting methanol to gasoline, e.g. as described in U.S. Pat. No. 3,894,107 to Butter et al. Although the market for gasoline is huge compared with the market for methanol, and although this process is currently used in New Zealand, it is complex and its viability appears to be limited to situations in which the cost for supplying an alternate source of gasoline is exceptionally high. There evidently remains a need for better ways to convert natural gas to higher valued and/or more readily transportable products.

A reaction which has been extensively studied is the direct partial oxidation of methane to methanol. This route, involving essentially the reaction of methane and gaseous oxygen according to the simple equation

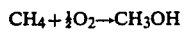

$$CH_4 + \tfrac{1}{2}O_2 \rightarrow CH_3OH$$

could theoretically produce methanol with no by-product. However, further oxidation of some of the methanol product to CO and $CO_2$ is usually observed. The homogeneous synthesis of methanol occurs most favorably under high pressure (10 to 200 atm.), moderate temperatures, (350°-500° C.), and at relatively low oxygen concentration to limit conversion. Oxidation of the methanol product to formaldehyde and to CO and $CO_2$ are minimized under these conditions. The mechanism of methanol formation is believed to involve the methylperoxy radical ($CH_3OO.$) which abstracts hydrogen from methane. Up until now the per pass yields of methanol from direct partial oxidation have been limited. This limited yield has been explained as due to the low reactivity of the C-H bonds in methane vis-a-vis the higher reactivity of the primary oxygenated product, methanol, which results in increased formation of the deep oxidation products CO and $CO_2$ when attempts are made to increase conversion.

Since it is known that methanol by itself can be catalytically converted to gasoline boiling range hydrocarbons with ZSM-5 type zeolites, the prospect of conducting this conversion during the direct partial oxidation of methane, i.e., redirecting the selectivity of the reaction from methanol to liquid hydrocarbons, is appealing. Previous investigators, however, have reported little success at significant redirection of selectivity.

Shepelev and Ione (React. Kinet. Catal. Lett., 1983, 23,323), found that mixtures of oxygen and methane in the presence of "ZSM" zeolites leads mainly to the formation of CO, $CO_2$ and $H_2O$ at 600° C. and atmospheric pressure. It appeared possible, however, to detect traces of ethane, ethylene, hydrogen and benzene. Studies at 100 atmosphere pressure and 400° C. indicated that a small amount of (unspecified) higher hydrocarbons formed. The methane and oxygen used were of 99.9% purity and reported free of higher hydrocarbons. However, U.S. Pat. 4,497,970 to D. Young discloses that such mixtures passed over zeolites under conditions similar to those used by Shepelev and Ione (ibid) formed only carbon oxides and water.

BRIEF DESCRIPTION OF THE DRAWING

FIG. 1. APPARATUS.

BRIEF SUMMARY OF THE INVENTION

We have now found that the purity of the hydrocarbon component critically determines whether methanol or liquid hydrocarbons are formed as the principal liquid product when the direct partial oxidation of methane is conducted in the presence of a crystalline zeolite catalyst exemplified by HZSM-5. In particular, we find that whereas methanol is selectively formed as the sole useful conversion product in the absence of impurity, in the presence of low concentrations of a reaction modifier, exemplified by propane or propylene, the selectivity is redirected from methanol to liquid hydrocarbons, all as more fully described hereinbelow.

DESCRIPTION OF THE INVENTION INCLUDING BEST MODE

In the practice of the present invention, it is preferred to use a dual flow system, i.e., a system in which the natural gas and the oxygen or air are kept separate until mixed just prior to being introduced into the reactor. However, if desired, the oxygen and natural gas may be premixed and stored together prior to the reaction. The preferred dual flow system minimizes the risk of fire or explosion. In the dual flow system, the amount of oxygen flow is controlled so as to prepare a reaction mixture that contains 2 to 20 percent by volume of oxygen, more preferably about 2 to 10 about percent. Air may be used instead of oxygen without affecting the reaction.

For purposes of the present invention, the GHSV (gas hourly space velocity) is within the range of about 100 to 50,000 $hr^{-1}$, preferably about 1000 to 10,000 $hr^{-1}$, and most preferably about 2000 to 5000 $hr^{-1}$. GHSV in all instances referred to herein means volume of feed per hour (at NTP, i.e., at 25° C. and 1 atm.) per volume of zeolite contained in the catalyst.

The temperature in the reaction zone is from about 300° C. to 500° C., and preferably about 350° C. to 450° C. In the preferred mode of operation, the reactor temperature is at least sufficiently high to cause substantially all of the oxygen to be consumed by the reaction, i.e., more than 90% of the oxygen in the feed, and preferably more than 95%.

The pressure in the reaction zone may be from 150 to 3,000 psig. Unreacted methone may be separated and recycled.

The apparatus shown in FIG. 1 of the drawing, which was used in the examples which follow, will now be described.

A methane source such as natural gas is fed via line 1 through valve 2 and passes via line 3 to a mass flow controller 4. It is then passed through check valve 5 and via line 6 passed to one arm of a mixing cross 7, another arm of which is fitted with a pressure gauge 14. The gaseous oxygen source is passed through line 8, through valve 9 and line 10 to mass flow controller 11, check valve 12 and then via line 13 to a third arm of the mixing cross 7. The mixed gasses exit the mixing cross 7 via the fourth arm, and pass through line 15 to mixing coil 16. The mixing coil consists of 40 feet of ⅛ inch O.D. tubing. The gas exits from the mixing coil and flows via line 17 which is fitted with a sand-filled filter 18, a T-fitting 19, a mass flow controller 20 and check valve 21. The gas mixture exiting from check valve 21 passes via line 22 to the inlet section of reactor 23 which is mounted in furnace 24. To maintain a constant pressure at the inlet to the reactor, one arm of the T-fitting 19 is connected to a Grove loader back pressure regulator 25 fitted with pressure gauge 26 and a bleed-off vent line 27. The pressure in line 22 and at the inlet to the reactor is indicated by pressure gauge 28. After passing through the Pyrex-lined reactor 23 mounted in furnace 24, hot gasses exiting the reactor pass via line 29 to a Grove loader back-pressure regulator 30 fitted with pressure gauge 31. The Grove loader is fitted with auxiliary line 32 and valves 34 and 35 connected to line 32 by a T-fitting. During start up of the run, valve 35 is closed and valve 34 is open, and the gasses exiting from the Grove loader are vented from valve 34 via line 33. After the temperature of the reactor has been adjusted, valve 34 is closed and the gasses passing from the Grove loader back-pressure regulator pass via line 37 to serially arranged cold traps 38, 39 and 40 via lines 41 and 42. Traps 38, 39, and 40 are maintained at dry ice temperature during a run. The cold gas is then passed via line 43 to gas sample bomb 44, and then via line 45 to wet test meter 46 from whence they are vented via line 47. Exit lines are heat-traced (not shown).

EXAMPLES

It is believed that this invention will be best understood by considering now the examples. In the examples which follow, analyses of the products formed was done by GC (gas chromatography) or by a combination of GC and MS (mass spectrometry).

A calibration procedure involving the analysis of known amounts of various hydrocarbons permitted the determination of the absolute GC response per gram of carbon. With this calibration, absolute amounts of feed and product methane could be calculated directly. Multiple product gas samples (at least 5) were collected during each run and analyzed by GC to verify that unit operation was steady. Sample-to-sample variations were minimal and the average value for all samples was used to calculate the overall gas product composition for the run.

Liquid products were also analyzed by GC. Absolute methanol determinations were accomplished by doping the liquid product with a known amount of ethanol as an internal standard. Positive identification of the small amounts of $C_2+$ water-soluble organic products which were often present was not attempted. However, GC and MS analyses indicated that the average elemental composition for these species was approximately 42% C, 7% H, and 51% O. Since these species were generally present in very small amounts, any imprecision in these values had little impact on the overall results. Their overall yield was calculated subject to the likely conservative assumption that their relative GC response weight factor was the same as that of the ethanol internal standard. Water was generally determined as the difference between the total aqueous liquid product weight and the methanol and $C_2+$ water-soluble organics weight. Measured elemental compositions were consistent with values calculated for the samples based on the GC methods described.

Carbon, hydrogen, and total material balances for the runs usually were at least 98%. The small amount of oxygen in the feed and associated low hydrocarbon conversions ("differential reactor" operation) resulted in oxygen balances of about 90%. Results were normalized on a no-loss-of-carbon basis. Conversion was calculated from the difference between the absolute amounts of the feed and product methane (and $C_3$ dopant, as applicable). Selectivities are based on grams of carbon in a given product as a percent of feed carbon converted.

When a separate liquid hydrocarbon layer was produced, it was analyzed by GC and GC/MS. Elemental determinations were also obtained.

The following examples are intended to illustrate the present invention without limiting the scope thereof, which scope is defined by this entire specification including appended claims. All amounts, proportions and selectivities shown are on a weight basis unless explicitly stated to be otherwise. A fresh portion of catalyst in the hydrogen form was used for each example. In the description which follows, HZSM-5 means the hydrogen form of a zeolite having the crystal structure of ZSM-5.

EXAMPLES 1-2 (Controls)

For these examples an HZSM-5 catalyst having a silica to alumina ratio of 70:1 was mixed with alumina (65% zeolite, 35% binder) and formed into extrudate. The extrudate (8.0 cc) was mixed with an equal volume of sand and loaded into the reactor's 9/16 inch I.D. pyrex glass liner insert.

In these examples feed mixtures were prepared from U.H.P. (ultra high purity) methane and C.P. grade oxygen supplied by Matheson, and the feed, with no reaction modifier, was passed over HZSM-5 catalyst. The oxygen contents differed in Examples 1 and 2, as did the total pressure and space velocities. These differences and the results of the experiments are included in Table II. It is evident from the data in Table II that methanol was the sole useful product, and that the presence of the HZSM-5 had no effect on the selectivity. The more severe conversion conditions of Example 2 resulted in small amounts of $C_2$–$C_4$ hydrocarbons being formed, but in neither example was liquid hydrocarbon detected.

TABLE I

Composition (vol. %) of Methane/n-$C_3$ Primary Standards and Commercial Natural Gas

| Component | Methane/n-$C_3$ Primary Standards | Commercial Natural Gas |
|---|---|---|
| $CH_4$ | 99.6 | 95.66 |
| Ethane | — | 2.46 |
| Propane | 0.4[1] | 0.33 |
| Butanes | — | 0.12 |
| $C_5$'s | — | 0.01 |
| $CO_2$ | — | 0.90 |
| $N_2$ | — | — |
| $H_2$ | — | 0.52 |
| | 100.00 | 100.00 |

[1]Propane or Propylene

EXAMPLES 3, 4 and 5

In these examples feed was prepared from methane/n-$C_3$ "primary standards" (composition shown in Table I) and C.P. grade oxygen supplied by Matheson. The oxygen content of the feed mixture and conversion conditions were the same as used in Example 1 except that the temperature was reduced by 10° C. to adjust for the observed 10° C. reduction in minimum temperature required for complete oxygen consumption. In Examples 3 and 4 the feed mixture contained 0.2 and 0.4 volume percent of propane as reaction modifier, and in Example 5 it contained 0.2 volume percent propylene.

It is evident from Table II that inclusion of 0.2 to 0.4 volume percent of propane or propylene in the feed drastically redirects the selectivity away from methanol (Example 1) to liquid hydrocarbons, mostly aromatic. In addition, small amounts of paraffins together with methanol and other water-soluble oxygenated compounds are formed.

A computation of product selectivities for all products (excluding the very small amount of methanol formed) based on the hypothesis that these arise solely from propane or propylene are summarized in Table II. The very high values, including values well over 100% for liquid hydrocarbons, show that methane must take part in forming these products when a $C_3$ modifier is present.

TABLE II

METHANE CONVERSION OVER ZSM-5

| Example No. | 1 | 2 | 3 | 4 | 5 | 6 |
|---|---|---|---|---|---|---|
| Catalyst | ZSM-5 | ZSM-5 | ZSM-5 | ZSM-5 | ZSM-5 | ZSM-5 |
| $SiO_2/Al_2O_3$ | 70:1 | 70:1 | 70:1 | 70:1 | 70:1 | 26:1 |
| Temp., °C. | 450 | 450 | 440 | 440 | 440 | 450 |
| Pressure, psig | 960 | 1400 | 960 | 960 | 960 | 960 |
| $C_3$ Type | — | — | $C_3^o$ | $C_3^o$ | $C_3^=$ | $C_3^o$ |
| $C_3$ Conc., vol % | — | — | 0.2 | 0.4 | 0.2 | 0.4 |
| $O_2$ Conc., vol % | 7.0 | 12.7 | 7.0 | 7.0 | 7.0 | 6.6 |
| GHSV, hr$^{-1}$ | 4600 | 3300 | 4600 | 4600 | 4600 | 4600 |
| $CH_4$ Conv., % | 5.2 | 8.8 | 4.4 | 4.1 | 4.5 | 5.3 |
| $C_3$ Conv., % | — | — | 42.0 | 47.3 | 64.1 | 55.6 |
| $O_2$ Conv., % | 100 | 100 | 100 | 100 | 100 | 100 |
| Total Carbon Conv., % | 5.2 | 8.8 | 4.6 | 4.6 | 4.8 | 5.9 |
| Product Selectivities (Based on Total Converted Carbon) | | | | | | |
| CO, % | 43.1 | 52.2 | 76.1 | 70.3 | 70.6 | 65.9 |
| $CO_2$, % | 40.2 | 36.4 | 12.7 | 11.4 | 13.7 | 17.0 |
| $CH_3OH$, % | 16.7 | 1.1 | 0.6 | 0.1 | 0.1 | 2.5 |
| Other Aq. Phase Oxygenates, % | — | 2.9 | 1.1 | 0.5 | 1.8 | 0.4 |
| $C_2$'s, % | — | 2.4 | 0.2 | 0.5 | — | 0.1 |
| $C_4$'s, % | — | 5.0 | 4.3 | 3.5 | 3.4 | 2.8 |
| Liquid HC Product, % | — | — | 4.9 | 13.7 | 10.5 | 11.3 |
| $C_2$–$C_4$ Yield, % | — | 0.7 | 0.2 | 0.2 | 0.2 | 0.2 |
| Liquid HC Yield, % | — | — | 0.2 | 0.6 | 0.5 | 0.7 |
| Product Selectivities (Based only on $C_3$ Converted Carbon; $CH_3OH$ assumed to come solely from $CH_4$.) | | | | | | |
| Other Aq. Phase Oxygenates, % | — | — | 21.1 | 3.8 | 22.0 | 3.7 |
| $C_2$'s, % | — | — | 3.5 | 3.8 | — | 0.5 |
| $C_4$'s, % | — | — | 82.5 | 28.8 | 41.7 | 25.9 |
| Liquid HC Product, % | — | — | 93.6 | 112.0 | 130.7 | 103.9 |

TABLE III

NATURAL GAS-HZSM-5 CATALYST

| Example No. | 7 | 8 |
|---|---|---|
| $SiO_2/Al_2O_3$ Ratio | 70:1 | 70:1 |
| Pressure, psig | 960 | 960 |
| Temperature, °C.[1] | 4201 | 4301 |
| GHSV, hr$^{-1}$ | 4600 | 4600 |
| $O_2$ in Feed, % | 6.7 | 13.9 |
| $CH_4$ Conv., % | 4.2 | 9.7 |
| $C_2$ Conv., % | 27.2 | 37.2 |
| $C_3$ Conv., % | 23.8 | 58.6 |
| $C_4$ Conv., % | 43.2 | 60.1 |
| Total Conversion Carbon Conv., % | 5.6 | 11.7 |
| Product Selectivities | | |
| $CO + CO_2$ | 83.0 | 93.7 |
| $CH_3OH$, plus other oxygenates | 0.8 | 1.7 |
| Liquid HC prod.[2] | 16.2 | 4.6 |

[1]Minimum temperature required for complete $O_2$ consumption.
[2]Typical hydrocarbon layer product distribution given in Table IV for Examples 3 to 8.

TABLE IV

Typical Hydrocarbon Layer Product Distribution

| Product | Wt. % |
|---|---|
| $C_5$—$C_8$ Paraffins & Olefins | 1.4 |

TABLE IV-continued

Typical Hydrocarbon Layer Product Distribution

| Product | Wt. % |
|---|---|
| Benzene, Toluene & Xylenes | 56.8 |
| C9+ Paraffins & Olefins | 0.1 |
| C9+ Aromatics | 23.7 |
| Unidentified | 18.0 |
| | 100.0 |

EXAMPLES 6, 7 and 8

Examples 6, 7 and 8 illustrate the effect of process variables on the product distribution. In Example 6 the silica alumina ratio was decreased for a propane-doped methane feed, while Examples 7-8 show the influence of increasing the oxygen content of the feed from about 7 volume percent to about 14 volume percent when processing natural gas the mixture of ethane, propane and butanes contained therein serving as reaction modifier. (See "Composition", given in Table I.)

The results obtained in Examples 6, 7 and 8 are included in Table II and in Table III. As can be seen from the data, decreasing the silica to alumina ratio has little impact on product selectivities, while increasing oxygen concentration markedly decreases production of desirable products.

Comparison of the results of Examples 3 to 8, inclusive, with Example 1 indicate that the effect of the reaction modifier is to redirect some of the conversion from methanol to other liquid compounds including benzene. The typical distribution of these "other" compounds is given in Table IV.

As illustrated by the foregoing examples, the method of this invention requires a feed mixture that contains a reaction modifier, and it further requires that conversion of the feed mixture be conducted in the presence of an intermediate pore size crystalline aluminosilicate zeolite catalyst having a silica to alumina ratio of at least about 12. The zeolite preferably has a silica to alumina ratio from about 15:1 to not more than about 70:1.

It is contemplated that a number of organic or inorganic compounds may serve as effective reaction modifiers in the present invention. Such compounds are exemplified in the recitation which follows:

ORGANIC (a) $C_2$-$C_{50}$ hydrocarbons including:
   n-paraffins such as ethane, propane, butane, pentane, and hexane
   n-olefins such as ethylene and propylene
   n-alkynes such as acetylene
   branched paraffins such as isobutane
   branched olefins such as isobutene
   branched alkynes
   diolefins
   naphthenes and alkylnaphthenes such as cyclopentane and cyclopenter
   aromatics and alkylaromatics such as benzene, toluene, xylene, naphthalene, and methylnaphthalene
(b) Others including:
   $C_1$-$C_{20}$ compounds including:
      alcohols such as methanol, ethanol, and propanol
      glycols such as ethylene glycol
      aldehydes such as formaldehyde and acetaldehyde
      carboxylic acids such as formic and acetic acid
      ethers such as dimethyl and diethyl ether
      esters such as ethyl acetate
      acid anhydrides such as maleic anhydride
      ketones such as acetone
      phenols
      epoxides
   (2) Compounds including:
      thiols such as methane thiol
      amines such as ethylenediamine and aniline
      phosphines such as trialkylphosphines
      amides such as acetamide
      nitriles such as acetonitrile
      thiocyanates
      disulfides such as dimethyldisulfide
      thioethers such as dimethylsulfide
      organohalides such as methyl chloride, ethyl, bromide, and methyl iodide
      sulfoxides, sulfones, and phosphene oxides
      organic derivatives of main group elements such as tetramethyl silane, trimethyl boron, and trialkyl aluminum
      organometal derivatives such as dimethylmercury, and tetraethyl lead
      organoesters of inorganic acids such as trimethyl borate, triethyl phosphate, and dimethyl sulfate
   (3) Compounds bearing 2 or more of the above functional groups.

INORGANIC (a) Halogens such as fluorine, chlorine, and bromine
(b) Non-metal oxides and sulfides such as NO, $NO_2$, $N_2O$, $H_2O_2$, $H_2S$, and $CS_2$
(c) Acids such as HF, HCl, and HBr
(d) Metal and non-metal halides such as $TiCl_4$, $SiCl_4$, $BF_3$, $BCl_3$, $AlCl_3$, $CCl_4$, and $PCl_3$
(e) Ammonia, phosphine, silane, and borane
(f) Oxyacids Preferred reaction modifiers are represented by the group of organic compounds consisting of paraffins, olefins, aromatics, and monohydric alcohols having two to about six carbon atoms, and mixtures thereof.

The class of intermediate pore size crystalline zeolites having a silica to alumina ratio of at least 12, and its characterization by a Constraint Index, has been described by Frilette, et al., Journal of Catalysis, vol. 67, No. 1, pp. 218-221 (January 1981) incorporated herein by reference for background. Members of this class which include ZSM-5, ZSM-11, ZSM12, ZSM-23, ZSM-35, ZSM-38, ZSM-48 and similar materials are contemplated as useful in the method of this invention.

The members of the above-described class of zeolites useful herein as catalyst component have an effective pore size of generally from about 5 to about 8 angstroms, such as to freely sorb normal hexane. In addition, the structure provides constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered are preferred, although, in some instances, excessive puckering of the rings or pore blockage may render these zeolites ineffective.

A convenient measure of the extent to which a zeolite provides controlled access to molecules of varying sizes to its internal structure is the Constraint Index (CI) of the zeolite. Zeolites which provide a highly restricted access to and egress from its internal structure have a high value for the Constraint Index, and zeolites of this kind usually have pores of small size, e.g. less than 5 angstroms. On the other hand, zeolites which provide relatively free access to the internal zeolite structure have a low value for the Constraint Index, and usually have pores of large size, e.g. greater than 8 angstroms. The method by which Constraint Index is determined is described fully in U.S. Pat. No. 4,016,218, incorporated herein by reference for details of the method.

Constraint Index (CI) values for some typical materials (some of which are outside the scope of the present invention are:

|  | CI (at test temperature) |
|---|---|
| ZSM-4 | 0.5 (316° C.) |
| ZSM-5 | 6–8.3 (371° C.–316° C.) |
| ZSM-11 | 5–8.7 (371° C.–316° C.) |
| ZSM-12 | 2.3 (316° C.) |
| ZSM-20 | 0.5 (371° C.) |
| ZSM-22 | 7.3 (427° C.) |
| ZSM-23 | 9.1 (427° C.) |
| ZSM-34 | 50 (371° C.) |
| ZSM-35 | 4.5 (454° C.) |
| ZSM-38 | 2 (510° C.) |
| ZSM-48 | 3.5 (538° C.) |
| ZSM-50 | 2.1 (427° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphouse silica-alumina | 0.6 (538° C.) |
| Dealuminized Y | 0.5 (510° C.) |
| Erionite | 38 (316° C.) |
| Zeolite Beta | 0.6–2.0 (316° C.–399° C.) |

The above-described Constraint Index is an important definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operations (conversion) and the presence or absence of binders. Likewise, other variables, such as crystal size of the zeolite, the presence of occluded contaminants, etc., may affect the Constraint Index. Therefore, it will be appreciated that it may be possible to so select test conditions, e.g. temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites, but that such values are the cumulative result of several variables useful in the determination and calculation thereof. Thus, for a given zeolite exhibiting a CI value within the range of 1 to 12, depending on the temperature employed during the test method within the range of 290° C. to about 538° C., with accompanying conversion between 10% and 60%, the CI may vary within the indicated range of 1 to 12. Likewise, other variables such as the crystal size of the zeolite, or the presence of possibly occluded contaminants and binders intimately combined with the zeolite, may affect the CI. It will accordingly be understood to those skilled in the art that the CI, as utilized herein, while affording a highly useful means for characterizing the zeolites of interest, is approximate, taking into consideration the manner of its determination, with the possibility, in some instances, of compounding variable extremes. However, in all instances, at a temperature within the above-specified range of 290° C. to about 538° C., the CI will have a value for any given zeolite of interest herein within the approximate range of 1 to 12.

The class of highly siliceous zeolites defined herein is exemplified by ZSM-5, ZSM-11, ZSM-12, ZSM-23, ZSM-35, ZSM-38, ZSM 48, and other similar materials.

U.S. Pat. No. 3,702,886 describing and claiming ZSM-5 is incorporated herein by reference.

ZSM-11 is more particularly described in U.S. Pat. No. 3,709,979, the entire content of which is incorporated herein by reference.

ZSM-12 is more particularly described in U.S. Pat. No. 3,832,449, the entire content of which is incorporated herein by reference.

ZSM-23 is more particularly described in U.S. Pat. No. 4,076,842, the entire content of which is incorporated herein by reference.

ZSM-35 is more particularly described in U.S. Pat. No. 4,016,245, the entire content of which is incorporated herein by reference.

ZSM-38 is more particularly described in U.S. Pat. 4,046,859, the entire content of which is incorporated herein by reference.

The specific zeolites described, when prepared in the presence of organic cations, are substantially catalytically inactive, possibly because the intra-crystalline free space is occupied by organic species from the forming solution. These organic templates are removed by heating in an inert atmosphere at 1000° F. for one hour, for example, followed by base exchange with ammonium salts followed by calcination at 1000° F. in air.

The zeolite may be incorporated with a matrix material (binder) to furnish a convenient form of M-2 forming catalyst, such as extrudate, for use in this invention. Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

A preferred crystalline zeolite for use in the present invention is ZSM-5 in the hydrogen form.

What is claimed is:

1. In a method comprising preparing a feed mixture of methane and oxygen gas or air, said mixture containing about 3 to about 15 volume percent $O_2$, and reacting said mixture at 150 to 3000 psig and at 350° to 500° C. whereby selectively forming said methanol, the improvement comprising, in combination:

including in said feed mixture an amount up to about 5 volume percent of a reaction modifier having 2 to 6 carbon atoms, said amount being effective to redirect said selectivity from methanol to-liquid hydrocarbons; and, reacting said feed mixture with included modifier in the presence of a catalyst comprising a crystalline aluminosilicate zeolite having a silica to alumina ratio of at least 12 and a Constraint Index of 1 to 12, thereby directly forming a mixture of organic compounds including unreacted methane and liquid hydrocarbons.

2. The method described in claim 1 wherein said reaction modifier is selected from the group consisting of paraffins, olefins, aromatics, monohydric alcohols, and mixtures thereof.

3. The method described in claim 2 wherein said reaction modifier propane or propylene.

4. The method described in claim 2 wherein said crystalline zeolite is selected from the group consisting of ZSM-5, ZSM-11, ZSM-12, ZSM-23, ZSM-35, ZSM-38 and ZSM-48.

5. The method described in claim 3 wherein said crystalline zeolite is selected from the group consisting of ZSM-5, ZSM-11, ZSM-12, ZSM-23, ZSM-35, ZSM-38 and ZSM-48.

6. The method described in claim 1 wherein said crystalline zeolite is HZSM-5 having a silica to alumina ratio not greater than about 70:1 and said feed mixture contains up to about 10 volume percent of oxygen gas.

7. The method described in claim 4 wherein said crystalline zeolite is HZSM-5 having a silica to alumina ratio not greater than about 70:1 and said feed mixture contains up to about 10 volume percent of oxygen gas.

8. The method described in claim 5 wherein said crystalline zeolite is HZSM-5 having a silica to alumina ratio not greater than about 70:1 and said feed mixture contains up to about 10 volume percent of oxygen gas.

9. The method described in claim 2 wherein said methane and at least a portion of said modifier are furnished by natural gas, and wherein said reaction temperature is at least sufficiently high as to cause consumption of substantially all of said oxygen in said feed.

10. The method described in claim 4 wherein said methane and at least a portion of said modifier are furnished by natural gas, and wherein said reaction temperature is at least sufficiently high as to cause consumption of substantially all of said oxygen in said feed.

11. The method described in claim 6 wherein said methane and at least a portion of said modifier are furnished by natural gas, and wherein said reaction temperature is at least sufficiently high as to cause consumption of substantially all of said oxygen in said feed.

12. The method described in claim 1 including the step of separating and recycling said unreacted methane.

* * * * *